US010159847B2

United States Patent
Rasmussen et al.

(10) Patent No.: US 10,159,847 B2
(45) Date of Patent: Dec. 25, 2018

(54) IMPLANTABLE MEDICAL DEVICES WITH ACTIVE COMPONENT MONITORING

(71) Applicant: Medtronic, Inc., Minneapolis, MN (US)

(72) Inventors: Marshall J. Rasmussen, Mesa, AZ (US); Lonny V. Cabelka, San Clemente, CA (US); Randolph E. Crutchfield, Scottsdale, AZ (US); Jon E. Zimmer, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 228 days.

(21) Appl. No.: 14/717,773

(22) Filed: May 20, 2015

(65) Prior Publication Data

US 2016/0339260 A1 Nov. 24, 2016

(51) Int. Cl.
*A61N 1/39* (2006.01)
*A61N 1/37* (2006.01)
A61N 1/36 (2006.01)

(52) U.S. Cl.
CPC ............. *A61N 1/3987* (2013.01); *A61N 1/37* (2013.01); *A61N 1/3956* (2013.01); *A61N 1/3975* (2013.01); *A61N 1/36142* (2013.01); *A61N 1/3937* (2013.01)

(58) Field of Classification Search
CPC .. A61N 1/3987; A61N 1/3975; A61N 1/3956; A61N 1/37; A61N 1/3937; A61N 1/36142
See application file for complete search history.

(56) References Cited

U.S. PATENT DOCUMENTS

| 4,332,256 A | 6/1982 | Brownlee et al. |
| 4,556,061 A | 12/1985 | Barreras et al. |
| 4,949,720 A | 8/1990 | Thompson |
| 5,103,427 A | 4/1992 | Erdol et al. |
| 5,137,020 A | 8/1992 | Wayne et al. |
| 5,163,428 A | 11/1992 | Pless |
| 5,188,105 A | 2/1993 | Keimel |
| 5,237,991 A | 8/1993 | Baker, Jr. et al. |
| 5,327,605 A | 7/1994 | Cragg |

(Continued)

FOREIGN PATENT DOCUMENTS

WO    2002053223 A3    10/2003

OTHER PUBLICATIONS (PCT/US2016/032977) PCT Notification of Transmittal of the International Search Report and the Written Opinion of the International Searching Authority.

*Primary Examiner* — Mark W Bockelman

(57) ABSTRACT

An implantable medical device includes a housing, a power source and an operational circuit that is coupled to the power source. The operational circuit includes a first electrode terminal and a second electrode terminal, an output circuit configured to deliver an electrical stimulation therapy through the first and second electrode terminals and a control circuit configured to evaluate an electrical parameter associated with the output circuit and to control generation of the electrical stimulation therapy responsive to a result of the evaluated parameter. Among other things, the implantable medical device may modify a parameter of the therapy delivery in response to a result of the evaluation.

17 Claims, 6 Drawing Sheets

(56) References Cited

U.S. PATENT DOCUMENTS

| | | | |
|---|---|---|---|
| 5,713,935 A * | 2/1998 | Prutchi | A61N 1/36521 |
| | | | 607/28 |
| 5,847,551 A | 12/1998 | Arora et al. | |
| 5,899,923 A | 5/1999 | Kroll et al. | |
| 6,067,470 A * | 5/2000 | Mower | A61N 1/3622 |
| | | | 607/5 |
| 6,549,807 B1 | 4/2003 | Kroll | |
| 6,553,263 B1 | 4/2003 | Kroll | |
| 6,898,463 B2 | 5/2005 | Dropps et al. | |
| 7,158,825 B1 | 1/2007 | Kroll et al. | |
| 8,086,312 B2 | 12/2011 | Nielsen et al. | |
| 8,417,333 B2 * | 4/2013 | Linder | A61N 1/3925 |
| | | | 600/547 |
| 2011/0245888 A1 | 10/2011 | Badelt et al. | |
| 2013/0238048 A1 | 9/2013 | Almendinger et al. | |
| 2013/0268025 A1 | 10/2013 | Ranu | |

* cited by examiner

IMPLANTABLE MEDICAL DEVICES WITH ACTIVE COMPONENT MONITORING

FIELD

The present disclosure relates to body implantable medical devices and, more particularly to circuits and techniques implemented in an implantable medical device to provide an electrical therapeutic output.

BACKGROUND

The human anatomy includes many types of tissues that can either voluntarily or involuntarily, perform certain functions. After disease, injury, or natural defects, certain tissues may no longer operate within general anatomical norms. For example, organs such as the heart may begin to experience certain failures or deficiencies. Some of these failures or deficiencies can be diagnosed, corrected or treated with implantable medical devices.

Implantable medical electrical leads are used with a wide variety of these implantable medical devices. The medical leads may be configured to allow electrodes to be positioned at desired cardiac locations so that the device can monitor and/or deliver stimulation therapy to the desired locations. For example, electrodes on implantable leads may detect electrical signals within a patient, such as an electrocardiogram, in addition to delivering electrical stimulation.

Currently, ICD's use endocardial or epicardial leads which extend from the ICD housing through the venous system to the heart. Electrodes positioned in or adjacent to the heart by the leads are used for pacing and sensing functions. Cardioversion and defibrillation shocks are generally applied between a coil electrode carried by one of the leads and the ICD housing, which acts as an active can electrode.

A subcutaneous implantable cardioverter defibrillator (SubQ ICD) differs from the more commonly used ICD's in that the housing and leads are typically implanted subcutaneously such that the sensing and therapy are accomplished subcutaneously. The SubQ ICD does not require leads to be placed in the heart or in contact with the heart. Instead, the SubQ ICD makes use of one or more electrodes on the housing, together with a subcutaneous lead that carries a defibrillation coil electrode and a sensing electrode.

The implantable medical devices are typically battery powered and often utilize capacitors or other electrical charge storage components to hold an electrical output to be made available to a patient. Due to the nature of defibrillation therapy or other high voltage therapy, it is not practical for the implantable medical device to supply the energy upon instantaneous demand by drawing from the power source. Instead, additional circuitry is provided to transfer and store the energy from the power source to accumulate a desired voltage level.

However, the placement of the SubQ ICD lead(s) and electrode(s) outside the heart presents a challenge to generating sufficient energy levels that are required to deliver appropriate therapy. As described herein, the present disclosure addresses the need in art to provide circuitry and techniques for generating appropriate electrical stimulation therapy in a SubQ ICD system.

SUMMARY

In accordance with aspects of this disclosure, circuits and techniques implemented in an implantable medical device are provided for generating an electrical stimulation therapy from a multi-cell power source. Therapy delivery by the implantable medical device is controlled as a function of an evaluation of a state of an operational circuitry of the implantable medical device.

In accordance with some embodiments, an implantable medical system comprises a housing, a power source disposed within the housing, and an operational circuit disposed within the housing and coupled to the power source, the operational circuit having (a) a first electrode terminal and a second electrode terminal, (b) an output circuit configured to deliver an electrical stimulation therapy through the first and second electrode terminals, and (c) a control circuit configured to evaluate an electrical parameter associated with the output circuit and to control generation of the electrical stimulation therapy responsive to a result of the evaluated parameter.

In further aspects of the embodiments of the present disclosure, the control circuit biases at least one component of the output circuit into a non-conducting state during the measurement of the electrical parameter.

In further aspects of the embodiments of the present disclosure, the control circuit is configured to perform a testing operation including controlling delivery of a sub-threshold electrical stimulation therapy through the output circuit to evaluate the electrical parameter based on the delivered sub-threshold electrical stimulation therapy.

In further aspects of the embodiments of the present disclosure, the control circuit is configured to evaluate the electrical parameter by performing a testing operation, including biasing at least one of the four interconnected switches in a conducting state, controlling delivery of the electrical stimulation therapy through the at least one biased switch to at least one of the first and second electrode terminals, and monitoring a voltage in response to delivered electrical stimulation therapy.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

As will be outlined in the present disclosure, techniques are employed to control therapy delivery by an implantable medical device (IMD) as a function of an evaluation of a state of an operational circuitry of the IMD. By way of example, an electrical parameter of one or more components of the operational circuitry may be monitored and evaluated. The IMD may modify a parameter of the therapy delivery in response to the evaluation of the leakage current.

Figure 1:
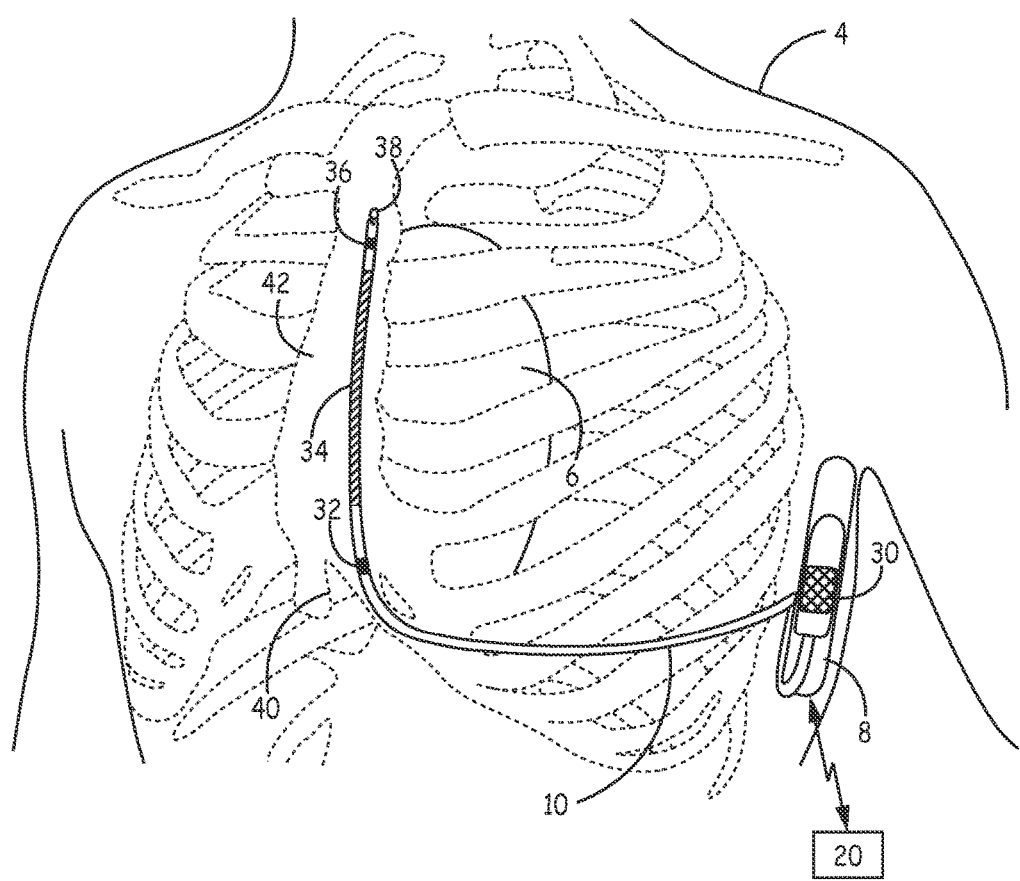
FIG. 1 is a conceptual diagram of a patient implanted with an example extravascular cardiac defibrillation system.

FIG. 1 is a conceptual diagram of a patient 4 implanted with an example extravascular cardiac defibrillation system 2. In the example illustrated in FIG. 1, extravascular cardiac defibrillation system 2 is an implanted subcutaneous defibrillation system. However, the techniques of this disclosure may also be utilized in other extravascular implanted cardiac defibrillation systems, such as a cardiac defibrillation system having a lead implanted at least partially in a substernal or submuscular location. Additionally, the techniques of this disclosure may also be utilized with other IMD systems, such as implantable cardioverter defibrillator systems, implantable cardiac resynchronization therapy (CRT) systems (e.g., CRT-P or CRT-D systems), implantable pacing systems, other implantable cardiac systems that include combinations of the cardiac systems above. Likewise the techniques may be used in non-cardiac implantable systems, including in implantable neurostimulation systems, drug delivery systems or other systems in which leads, catheters or other components are implanted at extravascular locations within patient 4. This disclosure, however, is described in the context of an implantable extravascular cardiac defibrillation system for purposes of illustration.

Extravascular cardiac defibrillation system 2 includes an implantable cardiac defibrillator (ICD) 8 connected to at least one implantable cardiac defibrillation lead 10. ICD 8 of FIG. 1 is implanted subcutaneously on the left side of patient 4. Defibrillation lead 10, which is connected to ICD 8, extends medially from ICD 8 toward sternum 42 and xiphoid process 40 of patient 4. At a location near xiphoid process 40 defibrillation lead 10 bends or turns and extends subcutaneously superior, substantially parallel to sternum 42. In the example illustrated in FIG. 1, defibrillation lead 10 is implanted such that lead 10 is offset laterally to the left side of the body of sternum 42 (i.e., towards the left side of patient 4).

ICD 8 includes a housing that forms a hermetic seal that protects components within ICD 8. The housing of ICD 8 may be formed of a conductive material, such as titanium or other biocompatible conductive material or a combination of conductive and non-conductive materials. In some instances, the housing of ICD 8 functions as an electrode 30 (sometimes referred to as a housing electrode or can electrode) that is used in combination with one of electrodes on the defibrillation lead 10 to deliver a therapy to heart 6 or to sense electrical activity, such as cardiac electrogram (EGM) signals, of heart 6. ICD 8 may also include a connector assembly (sometimes referred to as a connector block or header) that includes electrical feedthroughs through which electrical connections are made between conductors within defibrillation lead 10 and electronic components included within the housing. Housing may enclose one or more components, including processors, memories, transmitters, receivers, sensors, sensing circuitry, therapy circuitry and other appropriate components (often referred to herein as modules).

Defibrillation lead 10 includes a lead body having a proximal end that includes a connector configured to connect to ICD 8 and a distal end that includes one or more electrodes 36, 34, or 32. The lead body of defibrillation lead 10 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 10 is illustrated as including three electrodes 36, 34, or 32, defibrillation lead 10 may include more or fewer electrodes.

Defibrillation lead 10 includes one or more elongated electrical conductors (not illustrated) that extend within the lead body from the connector on the proximal end of defibrillation lead 10 to electrodes 36, 34, or 32. In other words, each of the one or more elongated electrical conductors contained within the lead body of defibrillation lead 10 may engage with respective ones of electrodes 36, 34, or 32. The connector at the proximal end of defibrillation lead 10 is connected to ICD 8 to electrically couple to circuitry, such as a therapy module or a sensing module, of ICD 8 via connections in connector assembly, including associated feedthroughs. The circuitry of ICD 8 is provided with electrode terminals that couple to the electrical conductors. The electrical conductors transmit therapy from the operational circuitry within ICD 8 to one or more of electrodes 36, 34 and 32 and transmit sensed electrical signals from one or more of electrodes 36, 34 and 32 to the sensing module within ICD 8.

Defibrillation lead 10 is placed along sternum 42 such that a therapy vector between a defibrillation electrode 34 and a second electrode (such as a housing or can electrode 30 of ICD 8 or an electrode placed on a second lead) is substantially across the ventricle of heart 6. The therapy vector may, in one example, be viewed as a line that extends from a point on the defibrillation electrode 34 to a point on the housing or can electrode 30 of ICD 8. In another example, defibrillation lead 10 may be placed along sternum 42 such that a therapy vector between defibrillation electrode 34 and the housing or can electrode 30 of ICD 8 (or other electrode) is substantially across an atrium of heart 6. In this case, extravascular ICD system 2 may be used to provide atrial therapies, such as therapies to treat atrial fibrillation.

The embodiment illustrated in FIG. 1 is an example configuration of an extravascular ICD system 2 and should not be considered limiting of the techniques described herein. For example, although illustrated as being offset laterally from the midline of sternum 42 in the example of FIG. 1, defibrillation lead 10 may be implanted such that lead 10 is offset to the right of sternum 42 or over sternum 42. Additionally, defibrillation lead 10 may be implanted such that it is not substantially parallel to sternum 42, but instead offset from sternum 42 at an angle (e.g., angled lateral from sternum 42 at either the proximal or distal end). As another example, the distal end of defibrillation lead 10 may be positioned near the second or third rib of patient 4. However, the distal end of defibrillation lead 10 may be positioned further superior or inferior depending on the location of ICD 8, location of electrodes 36, 34, and 32, or other factors.

Although ICD 8 is illustrated as being implanted near a midaxillary line of patient 4, ICD 8 may also be implanted at other subcutaneous locations on patient 4, such as further posterior on the torso toward the posterior axillary line, further anterior on the torso toward the anterior axillary line, in a pectoral region, or at other locations of patient 4. In instances in which ICD 8 is implanted pectorally, lead 10 would follow a different path, e.g., across the upper chest area and inferior along sternum 42. When the ICD 8 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 8 may sense electrical activity of heart 6 via one or more sensing vectors that include combinations of electrodes 36 and 32 and a housing or can electrode 30 of ICD 8. For example, ICD 8 may obtain electrical signals sensed using a sensing vector between electrodes 36 and 32, obtain electrical signals sensed using a sensing vector between electrode 36 and the conductive housing or can electrode 30 of ICD 8, obtain electrical signals sensed using a sensing vector between electrode 32 and the conductive housing or can electrode 30 of ICD 8, or a combination thereof. In some instances, ICD 8 may even sense cardiac electrical signals using a sensing vector that includes defibrillation electrode 34, such as a sensing vector between defibrillation electrode 34 and one of electrodes 32 or 36, or a sensing vector between defibrillation electrode 34 and the housing or can electrode 30 of ICD 8.

ICD may analyze the sensed electrical signals to detect tachycardia, such as ventricular tachycardia or ventricular fibrillation, and in response to detecting tachycardia may generate and deliver an electrical therapy to heart 6. For example, ICD 8 may deliver one or more defibrillation shocks via a therapy vector that includes defibrillation electrode 34 of defibrillation lead 10 and the housing/can electrode 30. Defibrillation electrode 34 may, for example, be an elongated coil electrode or other type of electrode. In some instances, ICD 8 may deliver one or more pacing therapies prior to or after delivery of the defibrillation shock, such as anti-tachycardia pacing (ATP) or post shock pacing. In these instances, ICD 8 may generate and deliver pacing pulses via therapy vectors that include one or both of electrodes 36 and 32 and/or the housing/can electrode. Electrodes 36 and 32 may comprise ring electrodes, hemispherical electrodes, coil electrodes, helix electrodes, segmented electrodes, directional electrodes, or other types of electrodes, or combination thereof. Electrodes 36 and 32 may be the same type of electrodes or different types of electrodes, although in the example of FIG. 1 both electrodes 36 and 32 are illustrated as ring electrodes.

Defibrillation lead 10 may also include an attachment feature 38 at or toward the distal end of lead 10. The attachment feature 38 may be a loop, link, or other attachment feature. For example, attachment feature 38 may be a loop formed by a suture. As another example, attachment feature 38 may be a loop, link, ring of metal, coated metal or a polymer. The attachment feature 38 may be formed into any of a number of shapes with uniform or varying thickness and varying dimensions. Attachment feature 38 may be integral to the lead or may be added by the user prior to implantation. Attachment feature 38 may be useful to aid in implantation of lead 10 and/or for securing lead 10 to a desired implant location. In some instances, defibrillation lead 10 may include a fixation mechanism in addition to, or instead of, the attachment feature. Although defibrillation lead 10 is illustrated with an attachment feature 38, in other examples lead 10 may not include an attachment feature 38. In this case, defibrillation lead 10 may be connected to or secured to an implant tool via an interference fit. An interference fit, sometimes also referred to as a friction fit, is a fastening between two parts which is achieved by friction after the parts are pushed together, rather than by any other means of fastening.

Lead 10 may also include a connector at the proximal end of lead 10, such as a DF4 connector, bifurcated connector (e.g., DF-1/IS-1 connector), or other type of connector. The connector at the proximal end of lead 10 may include a terminal pin that couples to a port within the connector assembly of ICD 8. In some instances, lead 10 may include an attachment feature at the proximal end of lead 10 that may be coupled to an implant tool to aid in implantation of lead 10. The attachment feature at the proximal end of the lead may separate from the connector and may be either integral to the lead or added by the user prior to implantation.

Defibrillation lead 10 may also include a suture sleeve or other fixation mechanism (not shown) located proximal to electrode 30 that is configured to fixate lead 10 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 2 may include more than one lead. In one example, extravascular cardiac defibrillation system 2 may include a pacing lead in addition to defibrillation lead 10.

In the example illustrated in FIG. 1, defibrillation lead 10 is implanted subcutaneously, e.g., between the skin and the ribs and/or sternum. In other instances, defibrillation lead 10 (and/or the optional pacing lead) may be implanted at other extravascular locations. In one example, defibrillation lead 10 may be implanted at least partially in a substernal location. In such a configuration, at least a portion of defibrillation lead 10 may be placed under or below the sternum in the mediastinum and, more particularly, in the anterior mediastinum. The anterior mediastinum is bounded laterally by pleurae, posteriorly by pericardium, and anteriorly by sternum. Defibrillation lead 10 may be at least partially implanted in other extra-pericardial locations, i.e., locations in the region around, but not in direct contact with, the outer surface of heart 6. These other extra-pericardial locations may include in the mediastinum but offset from sternum 42, in the superior mediastinum, in the middle mediastinum, in the posterior mediastinum, in the sub-xiphoid or inferior xiphoid area, near the apex of the heart, or other location not in direct contact with heart 6 and not subcutaneous.

Electrodes 36, 34, and 32 may comprise ring electrodes, hemispherical electrodes, coil electrodes, helical electrodes, ribbon electrodes, or other types of electrodes, or combinations thereof. Electrodes 36, 34, and 32 may be the same type of electrodes or different types of electrodes. In the illustrated example, electrode 34 is a coil electrode and electrodes 36 and 32 are ring, or hemispherical electrodes.

Also shown in FIG. 1 is medical device programmer 20, which is configured to program, and retrieve data from ICD 8. Programmer 20 may be a handheld computing device, desktop computing device, a networked computing device, etc. Programmer 20 may include a computer-readable storage medium having instructions that cause a processor of programmer 20 to provide the functions attributed to programmer 20 in the present disclosure. ICD 8 may wirelessly communicate with programmer 20. For example, ICD 8 may transfer data to programmer 20 and may receive data from programmer 20. Programmer 20 may also wirelessly program and/or wirelessly charge ICD 8. The programmer 20 may also issue an alert signal to notify a user in response to a measured electrical parameter of the ICD 8 as will be described in more detail below.

Data retrieved from ICD 8 using programmer 20 may include measurement data pertaining to components of the operational circuitry as will be described herein. Other examples include data pertaining to functionality of the ICD 8 or physiologic data such as cardiac EGMs stored by the ICD that indicates electrical activity of heart 6 and marker channel data indicating the occurrence and timing of sensing, diagnosis, and therapy events associated with ICD 8. Data transferred to ICD 8 using programmer 20 may include, for example, operational programs for the ICD 8 that causes the ICD to operate as described herein. Data transferred to the ICD 8 may include any programmable parameters of the ICD 8 or other IMDs described herein, such as the lengths of any intervals or delays described herein, the width and/or amplitude of the electrical pulses delivered by the other IMD, such as ICD 8, and the electrode vectors used by the IMDs to deliver and sense electrical pulses indicative of intrinsic depolarization of another chamber.

Figure 2:
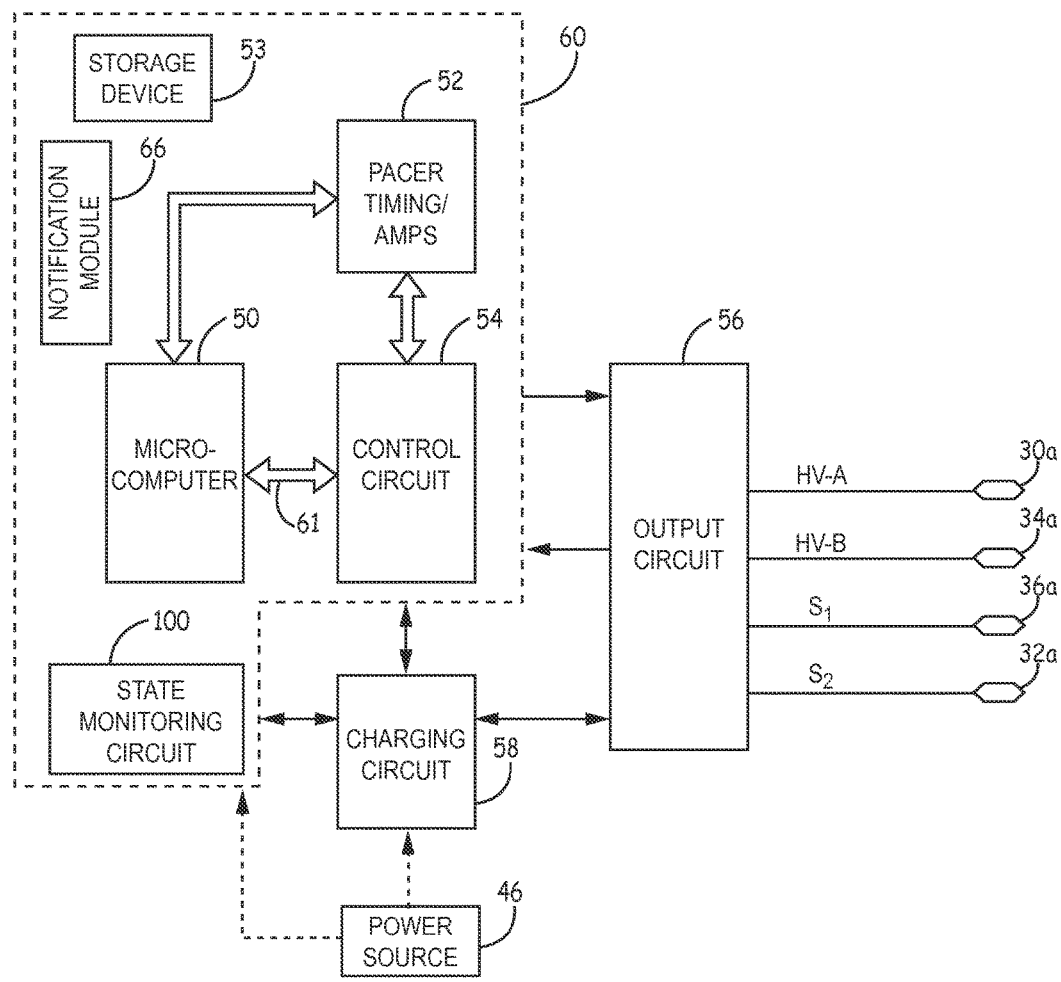
FIG. 2 is a schematic diagram of operational circuitry included in an exemplary extravascular cardiac defibrillation system according to an embodiment.

FIG. 2 is a schematic diagram of operational circuitry 48 included in ICD 8 according to an embodiment of the present disclosure. It is understood that the system of FIG. 2 includes both low power circuitry and high power circuitry. The present disclosure may be employed in a device that provides either or both of a high power electrical stimulation therapy, such as a high power defibrillation therapy, or a low power electrical stimulation therapy, such a pacing pulse, or both. Accordingly, the components in the operational circuitry 48 may support generation and delivery of either one or both such therapies. For ease of description, this disclosure will describe an operational circuitry 48 that supports only a high power electrical stimulation therapy, such as cardioversion and/or defibrillation stimulation therapy. However, it should be noted that the operational circuitry 48 may also provide defibrillation threshold (DFT) induction therapy, anti-tachycardia pacing (ATP) therapy, or post-shock pacing.

The operational circuitry 48 is powered by one or more power source(s) 46. The power source 46 may include a battery which may be rechargeable or non-rechargeable, an energy harvesting device, or any other energy source that can provide sufficient energy to power the functions of the ICD 8.

In the illustrative example, the ICD 8 functions are controlled by means of stored software, firmware and hardware that cooperatively monitor the cardiac electrical signals of the patient (e.g., EGM), determine when a cardioversion or defibrillation shock necessary, and deliver prescribed defibrillation therapies. The schematic diagram of FIG. 2 incorporates circuitry set forth, for example, in commonly assigned U.S. Pat. No. 5,103,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel, both incorporated herein by reference in their entireties, for selectively delivery of single phase, simultaneous biphasic and sequential biphasic cardioversion-defibrillation stimulation therapy. In an exemplary implementation, ICD 8 may deliver stimulation therapy employing housing electrode 30 coupled to the electrode node HV-A and at least one electrode such as electrode 34 coupled to the electrical node HV-B (at electrode terminals 30a and 34a, respectively) of the output circuit 56. In alternative embodiments, the ICD 8 may employ additional electrodes such as electrodes 32, 36 coupled to nodes such as S1, S2 (at terminals 32a and 36a, respectively) for sensing or stimulation therapy.

The cardioversion-defibrillation stimulation therapy energy and capacitor charge voltages can be intermediate to those supplied by implantable medical systems having at least one cardioversion-defibrillation electrode in contact with the heart and most AEDs having cardioversion-defibrillation electrodes in contact with the skin. The typical maximum voltage necessary for ICD 8 using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the waveform used. The ICD 8 of the present disclosure uses maximum voltages in the range of about 700 to about 3150 Volts and is associated with energies of about 25 Joules to about 210 Joules. The total high voltage capacitance could range from about 50 to about 74 microfarads.

Such cardioversion-defibrillation stimulation therapies are only delivered when a malignant tachyarrhythmia, e.g., ventricular fibrillation is detected through processing of the far field cardiac ECG employing one of the available detection algorithms known in the ICD 8 art.

In FIG. 2, pacer timing/sense amplifier circuit 52 processes the far field ECG SENSE signal that is developed across a particular ECG sense vector defined by a selected pair of the electrodes 30, 34, and optionally, electrodes 36, 32 if present as noted above. The selection of the sensing electrode pair is made through a control circuit 54 in a manner to provide the most reliable sensing of the EGM signal of interest, which would be the R wave for patients who are believed to be at risk of ventricular fibrillation leading to sudden death. The far field ECG signals are passed through the control circuit 54 to the input of a sense amplifier in the pacer timing/sense amplifier circuit 52.

Control circuit 54 may comprise one or more microprocessors, Application-Specific Integrated Circuits (ASICs), Digital Signal Processors (DSPs), Field-Programmable Gate Arrays (FPGAs), discrete electronic components, state machines, sensors, and/or other circuitry. Control circuit 54 may operate under the control of programmed instructions such as software and/or firmware instructions stored within a storage device 53. The storage device 53 may include volatile, non-volatile, magnetic, optical, and/or electrical media for storing digital data and programmed instructions, including Random Access Memory (RAM), Read-Only Memory (ROM), Non-Volatile RAM (NVRAM), Electrically Erasable Programmable ROM (EEPROM), flash memory, removable storage devices, and the like. These one or more storage devices 53 may store programs executed by control circuit 54.

Storage devices 53 may likewise store data, which may include, but is not limited to, programmed parameters, patient information, data sensed from the patient, and status information indicating the status of the ICD 8. For instance, the data may include statistical information and other characteristic data that is used to evaluate one or more components of the operational circuitry 48, such as the components of the output circuit 56, as will be discussed in more detail below.

Detection of a malignant tachyarrhythmia is determined via the control circuit 54 as a function of one or more sensed signals (e.g., R-wave signals and/or P-wave signals) that are output from the pacer timing/sense amplifier circuit 52 to the control circuit 54. An example detection algorithm is described in U.S. Pat. No. 7,103,404, titled "Detection of Tachyarrhythmia Termination", issued to Stadler, which is incorporated herein by reference in its entirety. Certain steps in the performance of the detection algorithm criteria are cooperatively performed in a microcomputer 50, including stored detection criteria that may be programmed into via a telemetry interface (not shown) conventional in the art.

The microcomputer 50 is generally representative of a processor and associated memory. The memory may reside internally within the microcomputer 50, or separately in storage device 53. The memory, for example, may include computer readable instructions that, when executed by processor, cause the operational circuitry and or any other component of the medical device to perform various functions attributed to them. For example, the memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, removable storage devices, or any other digital media for storing digital data and programmed instructions. Such memory will typically be non-transitory. The processor, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions attributed to the microcomputer 50 may be embodied as software, firmware, hardware, or any combination thereof.

Data and commands are exchanged between microcomputer 50 and control circuit 54, pacer timing/amplifier circuit 52, and output circuit 56 via a bi-directional data/control bus 61. The pacer timing/amplifier circuit 52 and the control circuit 54 are clocked at a slow clock rate. The microcomputer 50 is normally asleep, but is awakened and operated by a fast clock responsive to interrupts developed by sensed cardiac events or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 52.

The detection algorithms are highly sensitive and specific for the presence or absence of life threatening ventricular arrhythmias, e.g., ventricular tachycardia (V-TACH) and ventricular fibrillation (V-FIB). As discussed above, the detection algorithms contemplated in accordance with this disclosure may utilize sensed cardiac signals to detect the arrhythmias. In addition, detection algorithms for atrial fibrillation may also be included. The ICD 8 of the present disclosure includes the automatic detection and therapy of the most malignant rhythm disorders.

When a malignant tachycardia is detected, high voltage capacitors (FIG. 3) are charged to a pre-programmed voltage level by a charging circuit 58. It is generally considered inefficient to maintain a constant charge at all times on the high voltage capacitors. Instead, charging is initiated when control circuit 54 issues a high voltage charge command delivered to charging circuit 58 and charging is controlled by means of bi-directional signal line(s) from the HV output circuit 56. Without intending to be limiting, the high voltage output capacitors may comprise film, aluminum electrolytic or wet tantalum construction. Some examples of the high voltage output capacitors are described in commonly assigned U.S. Pat. No. 8,086,312, titled "Capacitors for Medical Devices", issued to Nielsen, which is incorporated herein by reference in its entirety.

The high voltage output capacitors may be charged to very high voltages, e.g., 700-3150V, to be discharged through the body and heart between the selected electrode pairs among first, second, and, optionally, third and/or fourth subcutaneous cardioversion-defibrillation electrodes 30, 34, 32, 36. The details of an exemplary charging circuit 58 and output circuit 56 will be discussed below. The high voltage capacitors are charged by charging circuit 58 and a high frequency, high-voltage transformer. The state of capacitor charge is monitored by circuitry within the output circuit 56 that provides a feedback signal indicative of the voltage to the control circuit 54. Control circuit 54 terminates the high voltage charge command when the received signal matches the programmed capacitor output voltage, i.e., the cardioversion-defibrillation peak shock voltage.

Control circuit 54 then develops a control signal that is applied to the output circuit 56 for triggering the delivery of cardioverting or defibrillating shocks. In this way, control circuitry 54 serves to control operation of the output circuit 56, which delivers high energy cardioversion-defibrillation stimulation therapies between a selected pair or pairs of the first, second, and, optionally, the third and/or fourth cardioversion-defibrillation electrodes 30, 34, coupled to the HV-A, HV-B and optionally to other electrodes such as electrodes 36, 32 coupled to the S1, S2 terminals as shown in FIG. 2.

Thus, ICD 8 monitors the patient's cardiac status and initiates the delivery of a cardioversion-defibrillation stimulation therapy through a selected pair or pairs of the first, second, third and/or fourth electrodes 30, 34, 36, and 32 in response to detection of a tachyarrhythmia requiring cardioversion-defibrillation.

Typically, the charging cycle of the capacitors has a short duration, e.g., it can take anywhere from two seconds to twenty seconds, and occurs very infrequently. The ICD 8 can be programmed to attempt to deliver cardioversion shocks to the heart in the example implementations described above in timed synchrony with a detected R-wave or can be programmed or fabricated to deliver defibrillation shocks to the heart in the example implementations described above without attempting to synchronize the delivery to a detected R-wave. Episode data related to the detection of the tachyarrhythmia and delivery of the cardioversion-defibrillation stimulation therapy can be stored in RAM for uplink telemetry transmission to an external programmer as is well known in the art to facilitate in diagnosis of the patient's cardiac state.

Housing 8 may include telemetry circuit (not shown in FIG. 2), so that it is capable of being programmed by means of external device 20 (FIG. 1) via a 2-way telemetry link as is known in the art. Uplink telemetry allows device status and diagnostic/event data to be sent to external programmer for review by the patient's physician. Downlink telemetry allows the external programmer via physician control to allow the programming of device function and the optimization of the detection and therapy for a specific patient. Programmers and telemetry systems suitable for use in the practice of the present disclosure have been well known for many years. Known programmers typically communicate with an implanted device via a bi-directional telemetry link such as Bluetooth®, radio-frequency, near-field, or low frequency, so that the programmer can transmit control commands and operational parameter values to be received by the implanted device, and so that the implanted device can communicate diagnostic and operational data to the programmer.

Those skilled in the art will appreciate that the various components of the low power circuit 60 e.g., pacer/sense circuit 52, control circuit 54, and microcomputer 50 are illustrated as separate components for ease of discussion. In alternative implementations, the functions attributed to the components of the low power circuitry 60 may suitably be performed by a sole component.

Operational circuitry 48 further includes a state monitoring circuit 100 that is configured to evaluate the condition of one or more components of the output circuit 56. The monitoring circuit 100 measures an electrical parameter of one or more of the components of the output circuit 56 for an evaluation to detect a potential failure state or actual failure state. By way of example, the electrical parameter measured by the monitoring circuit 100 may comprise a leakage current flowing through one or more components of the output circuit 56. In another example, the electrical parameter measured by the monitoring circuit 100 may comprise a voltage across one or more components of the output circuit 56. The results of the evaluation of the electrical parameter may trigger the control circuit 54 may modify a therapy delivery regimen in response to the result of the evaluation of the electrical parameter. In an alternative embodiment, the functionality of the monitoring circuit 100 may be implemented within the control circuit 54. As such, the control circuit 54 will evaluate the state of the output circuit 56 and modify control therapy delivery by the ICD 8 as a function of the evaluation of the state of the output circuit 56.

A notification module 66 issues a notification to a user such as the patient 4. The notification may include an audible warning, a vibration, a mild electrical stimulus, or some combination of these warnings. In addition, the notification may include transmission of a radio signal to a programmer or an external device, such as a transceiver that responds by contacting a physician by telephone, paging, or electronic mail. Additionally, control circuit 54 may automatically activate life-critical features, such as ventricular fibrillation detection and therapy in response to detection of a potential or actual failure state.

Figure 3:
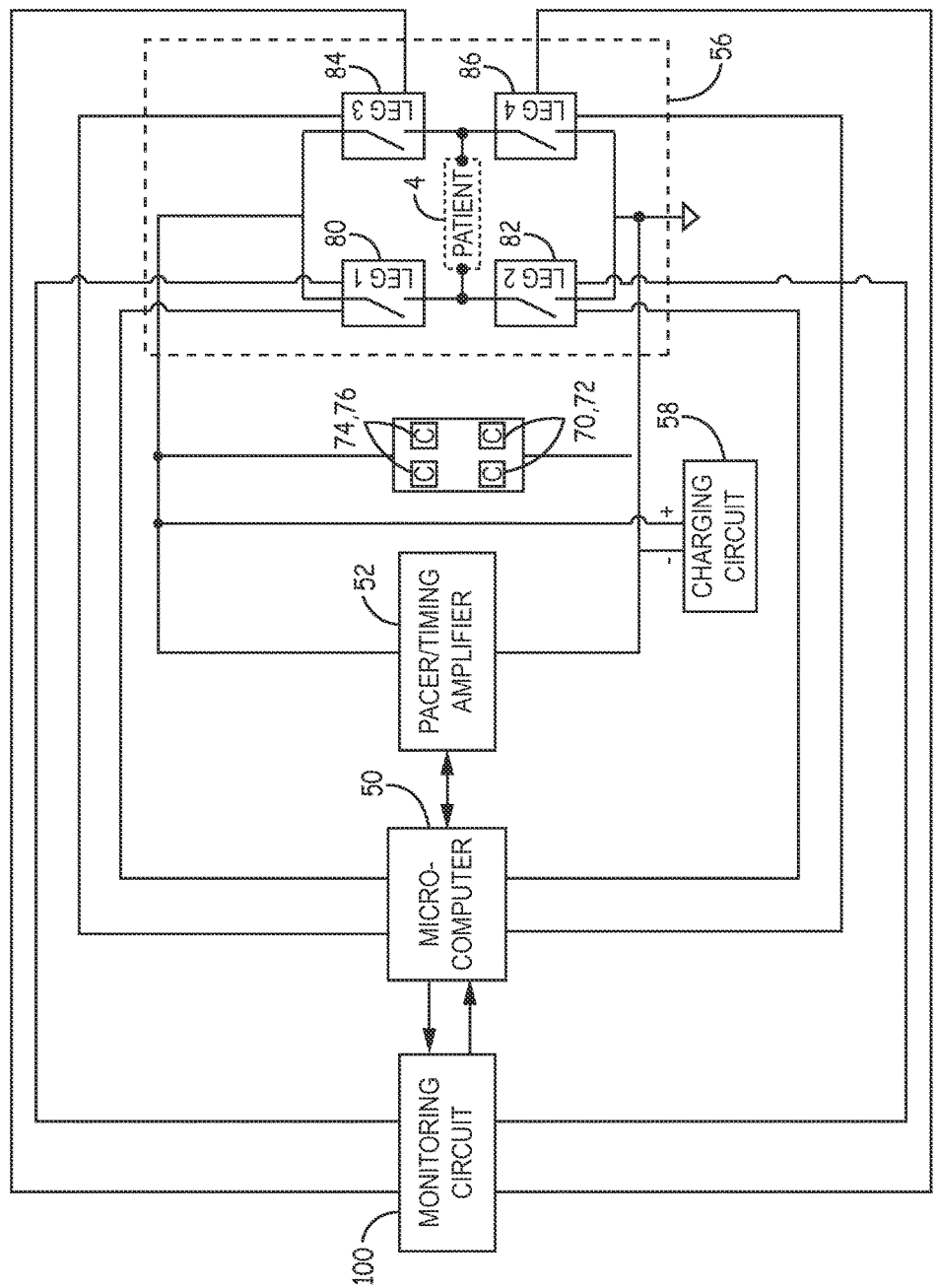
FIG. 3 illustrates an exemplary schematic showing a portion of the operational circuitry of FIG. 2 in accordance with an embodiment of the disclosure.

FIG. 3 illustrates an exemplary schematic showing a portion of the operational circuitry of FIG. 2, in accordance with an embodiment of the disclosure, in greater detail. The output circuit 56 allows the controlled transfer of energy from the energy storage capacitors 70, 72, 74, and 76 to the patient 4.

The output circuit 56 includes four switches 80, 82, 84, and 86 that are interconnected. The interconnection of the four switches comprises the switches 80 and 82 being configured in a parallel orientation alongside switches 84 and 86 and a bridge being provided to intersect each of the pair of parallel connected switches. As is shown in FIG. 3, the interconnected switches are arrayed to define an orientation that includes a high side pair of switches 80 and 84 and a low side pair of switches 82 and 86 in a configuration that may resemble a "H". In other words, the four interconnected switches are arrayed having switches 80 and 84 defining the high side of the H-bridge and switches 82 and 86 defining the low side of the H-bridge.

The intersecting bridge includes two terminals that couple the output circuit 56 to the electrodes 30 and 34. As previously described, patient 4 is connectable (e.g., using leads/electrodes 30, 32 and any other suitable connections) between terminal HV-A located between the switch 80 and switch 82 and terminal HV-B located between switch 84 and switch 86.

Although FIG. 3 is illustrated with four switches thereby providing two terminals, it should be noted that the output circuit 56 is not limited to four switches. In other embodiments, the output circuit 56 may include six switches for three output terminals, or eight switches for four output terminals, or any other number of switches based on the desired number of output terminals. Of course, additional modifications to the circuits of this disclosure would be made to accommodate such changes, but such modifications are within the comprehension of those skilled in the art having the benefit of this disclosure.

Switches 80 and 84 are coupled to a positive terminal of the energy storage capacitors 70, 72, 74, and 76. Unlike conventional output circuits which include a discharge switch that is coupled between the H-Bridge switches and energy storage capacitors, the present disclosure is provide without the discharge switch. Switches 82 and 86 are coupled to a negative terminal of the energy storage capacitors 70, 72, 74, and 76. The biasing into a conducting or non-conducting state of one or more of the switches 80, 82, 84, 86 may be controlled by control signals issued by control circuit 54. For example, control signals to bias one or more of switches 80, 82, 84, 86 into a conducting state may be issued to configure the H-bridge in one or more configurations to provide one or more types of stimulation pulses, or may be used to provide active or passive recharge, etc.

For example, in accordance with an embodiment, the ICD 8 provides a biphasic defibrillation pulse to the patient in the following manner. With reference to FIG. 3, once the energy storage capacitors 70, 72, 74, and 76 are charged to a selected energy level, the switches 80 and 86 are closed so as to provide a path from the capacitors 70-76 to electrodes 30, 34 for the application of a first phase of a defibrillation pulse to the patient 4. The stored energy travels from the positive terminal of the capacitors, through switch 80, across the patient 4, back through switch 86 to the negative terminal of the capacitors 70-76. The first phase of the biphasic pulse therefore applies a positive pulse from the electrode 30 to the electrode 34.

Before the energy storage capacitors 70, 72, 74, and 76 are completely discharged, switch 86 is biased off in preparation for application of the second phase of the biphasic pulse. Once switch 86 is biased off, switch 80 will also become non-conducting because the current flowing through it falls to below its holding current.

After the end of the first phase of the biphasic defibrillation pulse, the switches 84 and 82 are switched on to start the second phase of the biphasic pulse. Switches 84 and 82 provide a path to apply a negative defibrillation pulse to the patient 4. With reference to FIG. 3, the energy travels from the positive terminal of the capacitors 70, 72, 74, and 76, through switch 84, across the electrodes 34, 30 coupled to the patient 4, and out through switch 82 to the negative terminal of the capacitors 70, 72, 74, and 76. The polarity of the second phase of the defibrillation pulse is therefore opposite in polarity to the first phase of the pulse.

As described in reference to FIG. 3, the four output switches 80, 82, 84 and 86 allow the transfer of energy from the energy storage capacitors 70, 72, 74, and 76. Switches 80 and 84 may be provided as a combination of solid-state semiconductor devices, such as a MOSFET-triggered anode gated thyristor (AGT), with the MOSFET being connected to the gate of the AGT. In such an embodiment, the MOS- FET is controlled by the control circuit 54 from a conducting to a non-conducting state. Switches 82 and 86 are both solid-state semiconductor switches, such as insulated gate bipolar transistors (IGBT). In other embodiments, any one of the switches 80-86 may be embodied as any known solid-state semiconductor switching device including AGT, FET, IGBT, or silicon controlled rectifier (SCR). The four output switches 80 to 86 can be switched from an off (non-conducting) to an on (conducting) condition based on control signals provided by the control circuit 54. Switches 80 to 86 remain in a conducting state as long as the control signal provided by the control circuit 54 is present.

Each of the switches 80, 82, 84, and 86 is coupled to a monitoring circuit 100. The monitoring circuit 100 is configured to perform a testing operation that includes measuring an electrical parameter of the switches 80-86. The electrical parameter may include a current flowing through one or more of the switches 80-86 or a voltage across one or more of the switches 80-86. For ease of illustration, the electrical parameter described in embodiments of the present disclosure will be considered to be a current flowing through the switches 80-86.

In an embodiment, the control circuit 54 is configured to perform the testing operation by controlling delivery of a stimulation therapy pulse or a sub-threshold electrical stimulation pulse through the output circuit 56. In contrast to the stimulation therapy pulse, the sub-threshold electrical stimulation pulse is a non-capturing electrical stimuli that is configured (e.g., too low amplitude and/or pulse width, etc.) so as not to generate an evoked response when delivered to the heart. During the testing operation, the control circuit 54 may bias the one or more of switches 80-86 that is being monitored into a non-conducting state prior to and/or during the measurement of the electrical parameter. In another embodiment, the testing operation to assess the condition of the switches 80-86 may be performed while the switches 80-86 are biased in a conducting state.

The inventors of the present disclosure have observed that a typical solid-state semiconductor switching device such as an SCR and IGBT in some applications may have a leakage current of around 1 milliamp. The solid-state semiconductor switching devices, such as the switches 80-86 of this disclosure rely on gate voltages to control the current flow. Without intending to be bound by theory, the inventors believe that the amount of leakage current flowing through one or more of the switches 80-86 may change during the operation of the ICD 8. Changes in the amount of the leakage current flowing through the switches 80-86 may impact the delivery of therapy to the patient and affect the operation and functions of the ICD 8. Depending on the magnitude of the change in the leakage current, a failure state of the ICD 8 may arise.

The measurement of the electrical parameter by the monitoring circuit 100 may be performed across a load, such as heart 6 of the patient. The output circuit 56 may be controlled to deliver an electrical pulse, such as a therapy stimulation pulse or a sub-threshold stimulation pulse. The current flowing through one or more of the switches 80-86 may be determined by, for example, measuring the voltage across a known load such as the heart 6.

The measured electrical parameter (for example, the leakage current) of one or more switches 80-86 of the output circuit 56 is utilized to detect a potential or actual failure state. The monitoring circuit 100 may be coupled to the control circuit 54 for transmission of the measured electrical parameter. The control circuit 54 evaluates the measured electrical parameter and utilizes the result of the evaluation of the electrical parameter to determine whether to modify a therapy delivery regimen. For example, the modification may comprise increasing the stimulation threshold of a stimulation therapy that is to be delivered to patient 4. In another example, an alert signal may be generated responsive to the results of the evaluation as described, for example, in U.S. Pat. No. 6,082,367 and telemetered to a user in response to the result of the evaluation of the electrical parameter. In another example, an alert signal may be issued by the notification module 66 to alert a user such as patient 4 of the potential or actual failure in response to the result of the evaluation of the electrical parameter. As previously mentioned, the functionality of the monitoring circuit 100 may be implemented within the control circuit 54. As such, the control circuit 54 may measure and evaluate the parameter of the one or more switches 80-86 and modify or control delivery of therapy by the ICD 8 as a function of the evaluation of the one or more switches 80-86.

Figure 4:
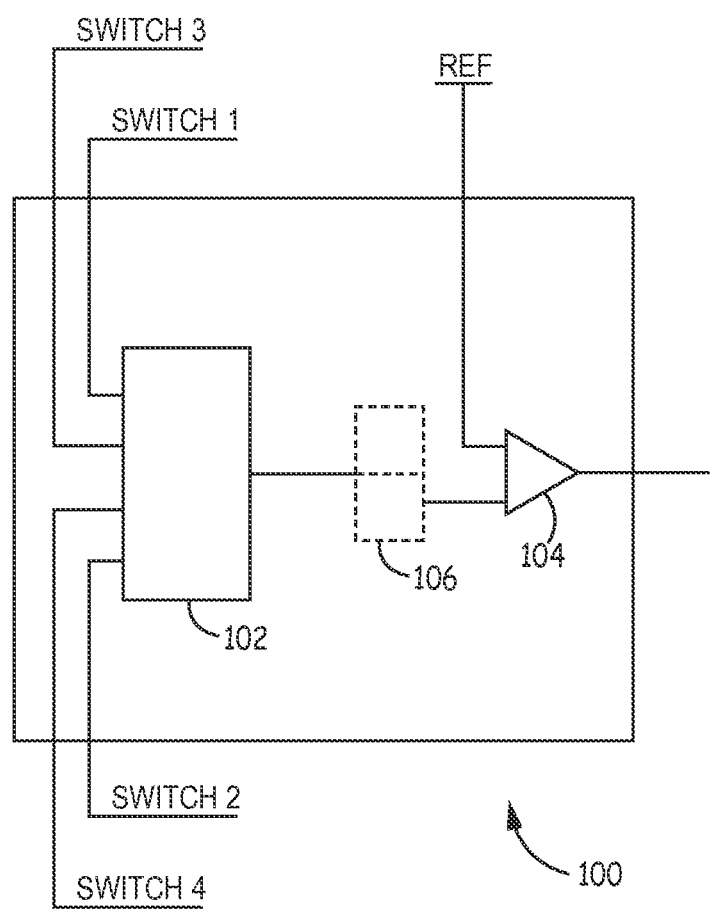
FIG. 4 depicts an exemplary monitoring circuit provided for evaluating an electrical parameter of an output circuit of an exemplary extravascular cardiac defibrillation system.
Figure 5:
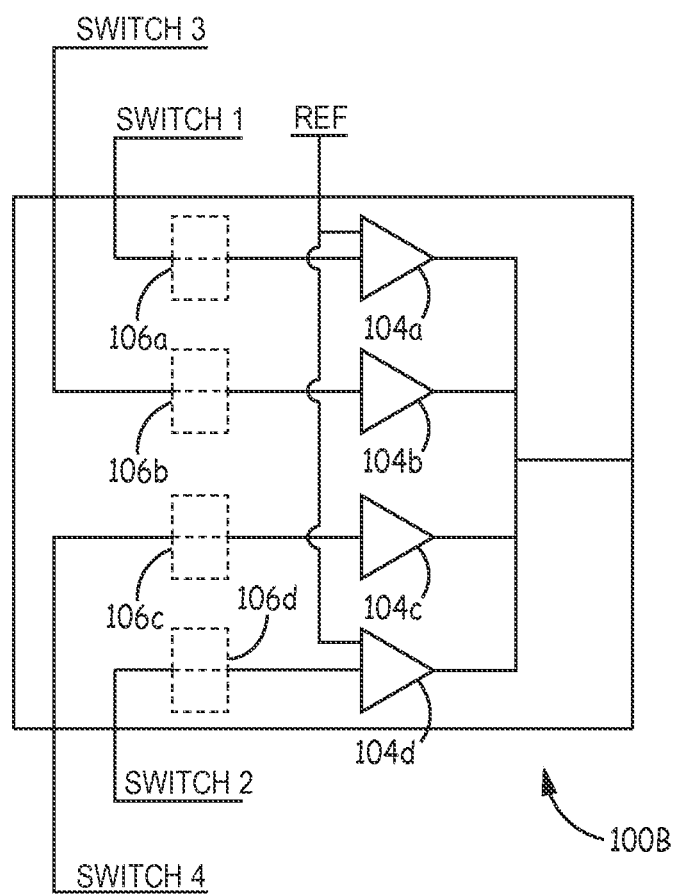
FIG. 5 depicts an exemplary monitoring circuit provided for evaluating an electrical parameter of an output circuit of an exemplary extravascular cardiac defibrillation system.

Referring to FIGS. 4 and 5, an exemplary monitoring circuit is provided for evaluating an electrical parameter of an output circuit 56 of the ICD 8. In FIG. 4, the monitoring circuit 100*a* includes a multiplexer 102, and a comparator 104.

As depicted in FIG. 4, signal lines (Switch 1-4) from each of the interconnected switches 80-84 are coupled to the multiplexer 102. The multiplexer 102 selects one of the signal lines from a respective one of the switches 80-84 as the first input voltage to the comparator 104. A reference signal (REF) is provided as the second input voltage into comparator 104. The reference signal provides a predefined voltage signal against which the selected first input voltage is compared. For example, the predefined voltage may correspond to the maximum amount of leakage current that can flow through a given one of the switches 80-84 without impacting the operation of the ICD 8. In an example, such reference signal values may be determined empirically and stored in storage device 53.

The comparator 104 is configured to compare the magnitude of the selected first input voltage and the magnitude of the second input voltage. Then, as a result of the comparison, the comparator 104 outputs information about which one of the magnitudes is greater, as one digital value.

In an alternative embodiment, a voltage converter 106 may optionally be included to convert the leakage current flowing across the selected one of the switches 80-86 into a voltage prior to input into the comparator 104.

In the alternative embodiment of FIG. 5, the monitoring circuit 100*b* may be embodied to include a plurality of comparators 104*a-d* such that each of the signal lines (Switch 1-4) is coupled to a dedicated one of the plurality of comparators 104*a-d*. In doing so, the multiplexer 102 may be rendered unnecessary. Voltage converter 106*a-d* may optionally be included to convert the leakage current flowing across the selected one of the switches 80-86 into a voltage prior to input into the comparator 104. Such a configuration facilitates simultaneous evaluation of the plurality of components (e.g., switches 80-84).

Figure 6:
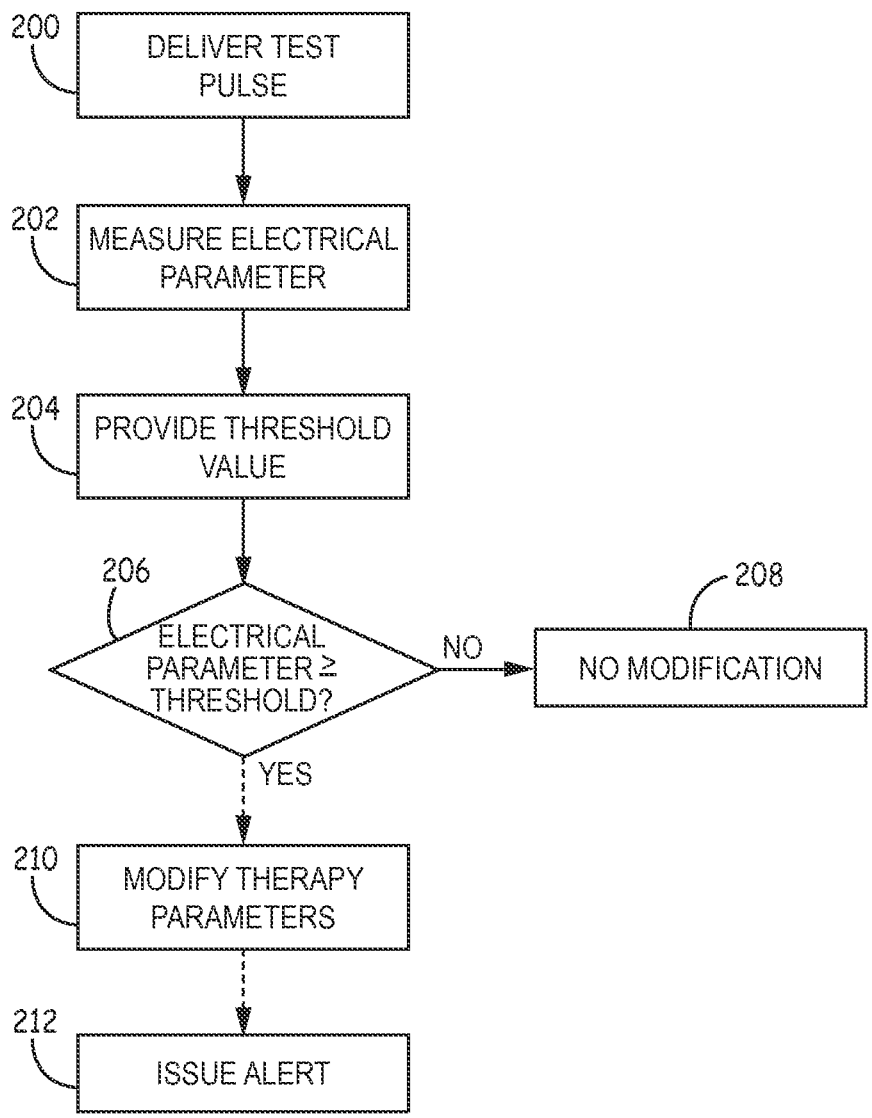
FIG. 6 shows a flowchart depicting the method tasks of an exemplary embodiment of a technique that is employed to control therapy delivery by an exemplary extravascular cardiac defibrillation system.

Turning now to FIG. 6, a flowchart is shown depicting the method tasks of an exemplary embodiment of a technique that is employed to control therapy delivery by an implantable medical device such as ICD 8 as a function of an evaluation of a condition of components of operational circuitry of the ICD 8.

The method is initiated by delivering an electrical test pulse through the operational circuitry of the ICD 8 (200). The test pulse may comprise a therapy stimulation pulse or a sub-threshold stimulation pulse.

In response to delivering the test pulse, an electrical parameter of a component of the operational circuitry is measured (202). For example, the electrical parameter may comprise a current flowing through one or more of the switches 80-86. In another example, the electrical parameter may comprise a voltage across a known load, such as the heart 6. The electrical parameter may be measured as described, for example, in conjunction with the state monitoring circuit 100 in FIGS. 2-5.

A predetermined threshold value for the component(s) being assessed is provided (204). The predetermined threshold value may correspond to a potential or actual failure state of the component(s). For example, the components of the operational circuitry may include a switch. In that example, the predetermined threshold value will correspond to a leakage current value that represents the greatest amount of leakage current that can flow through the switch while maintaining appropriate functionality of the operational circuitry 48.

The measured electrical parameter is evaluated to assess a state of an operational circuitry (206). The evaluation may comprise comparing the magnitude of the measured electrical parameter to the predetermined threshold value.

In response to the results of the evaluation of the electrical parameter being less than, or equal to, the threshold, the functionality of the ICD 8 will not be changed (208). For example, the ICD 8 may continue to deliver therapy at the pre-existing parameters.

However, responsive to the results of the evaluation of the electrical parameter being greater than the threshold, the functionality of the ICD 8 may be changed. For example, the ICD 8 may modify one or more therapy delivery parameters as discussed above in one embodiment (210). In an alternative embodiment, or in addition, the ICD 8 may issue an alert to notify a user such as the patient or a clinician about the detected potential or actual failure (212). The flow to tasks 210 and 212 is shown in dotted lines to illustrate that both tasks need not be present, but rather that one or both may be employed in a given ICD 8.

Embodiments of the method as described in FIG. 6 may be implemented as a computer-implemented method or computer-implemented instructions stored in a memory, such as the memory devices described above, that, when executed by processor (solely, or in conjunction with firmware or hardware), cause the operational circuitry and or any other component of the medical device to perform various functions attributed to them.

What is claimed is:

1. An implantable medical system, comprising:
a housing;
a power source disposed within the housing; and
an operational circuit disposed within the housing and coupled to the power source, the operational circuit comprising:
  a first electrode terminal and a second electrode terminal,
  an output circuit configured to deliver an electrical stimulation therapy through the first and second electrode terminals, wherein the output circuit includes at least four interconnected switches arrayed having a high side and a low side, wherein each of the at least four interconnected switches is configurable to be biased between a non-conducting state and a conducting state, and wherein at least two of the at least four interconnected switches is biased to a conducting state when electrical stimulation therapy is delivered through the first and second electrode terminals,
  one or more capacitors coupled to and configured to be charged using the power source and coupled to the output circuit, the one or more capacitors being configured to store energy for discharge and delivery of the electrical stimulation therapy through the output circuit, and
  a control circuit configured to:
    issue a charge command to initiate charging of the one or more capacitors with each of the at least four interconnected switches in a non-conducting state, wherein each of the at least four interconnected switches in the non-conducting state has a leakage current flowing through the switch,
    measure and evaluate an electrical parameter associated with the output circuit, wherein the control circuit biases the at least four interconnected switches into the non-conducting state during the measurement of the electrical parameter, wherein the measured electrical parameter is based on a leakage current flowing through at least one of the at least four interconnected switches biased in the non-conducting state and measured across a load comprising the heart, and
    once the one or more capacitors are charged to a selected energy, issue a control signal to trigger discharge and delivery of the electrical stimulation therapy through the output circuit by biasing two or more of the switches into a conducting state, wherein the generation of electrical stimulation therapy is controlled responsive to a result of the evaluated parameter.

2. The implantable medical system of claim 1, the high side having a first switch and a third switch and the low side having a second switch and a fourth switch, wherein the first electrode terminal is coupled between the first and second switches and the second electrode terminal is coupled between the third and fourth switches, and further wherein each of the four interconnected switches comprises a solid-state semiconductor device.

3. The implantable medical system of claim 2, wherein the first and third switches comprise anode gated thyristors (AGT) and the second and fourth switches comprise insulated gate bipolar transistors (IGBT).

4. The implantable medical system of claim 1, further comprising a monitoring circuit coupled to the control circuit, the monitoring circuit being configured to measure the electrical parameter of the output circuit, wherein the monitoring circuit includes a voltage comparator configured to evaluate the electrical parameter of at least one component of the output circuit.

5. The implantable medical system of claim 1, further comprising a lead coupled to the housing, the lead including at least a first electrode coupled to the first electrode terminal.

6. The implantable medical system of claim 1, further comprising:
at least a third electrode terminal, and
a lead coupled to the housing, the lead including at least a first electrode and a second electrode coupled to the first and second electrode terminals respectively.

7. The implantable medical system of claim 1, further comprising a second electrode coupled to the housing, the second electrode being coupled to the second electrode terminal.

8. The implantable medical system of claim 1, wherein the high side is coupled to a terminal of the one or more capacitors without any additional switch coupled between the high side and the one or more capacitors.

9. An implantable medical system, comprising:
   a housing;
   a power source disposed within the housing; and
   an operational circuit disposed within the housing and coupled to the power source, the operational circuit comprising:
      a first electrode terminal and a second electrode terminal,
      an output circuit configured to deliver an electrical stimulation therapy through the first and second electrode terminals, wherein the output circuit includes at least four interconnected switches arrayed having a high side and a low side, wherein each of the at least four interconnected switches is configurable to be biased between a non-conducting state and a conducting state, and wherein at least two of the at least four interconnected switches is biased to a conducting state when electrical stimulation therapy is delivered through the first and second electrode terminals,
      one or more capacitors coupled to and configured to be charged using the power source and coupled to the output circuit, the one or more capacitors being configured to store energy for discharge and delivery of the electrical stimulation therapy through the output circuit, wherein the high side of the output circuit is coupled to a terminal of the one or more capacitors without any additional switch coupled between the high side and the one or more capacitors, and
      a control circuit operably coupled to the first electrode terminal and the second electrode terminal to measure and evaluate an electrical parameter associated with the output circuit, the control circuit configured to:
         issue a charge command to initiate charging of the one or more capacitors with each of the at least four interconnected switches in a non-conducting state, wherein each of the at least four interconnected switches in the non-conducting state has a leakage current flowing through the switch,
         measure and evaluate the electrical parameter from the first electrode terminal and the second electrode terminal, wherein the control circuit biases the at least four interconnected switches into the non-conducting state during the measurement of the electrical parameter, wherein the measured electrical parameter is based on a leakage current flowing through at least one of the at least four interconnected switches biased in the non-conducting state, and
         once the one or more capacitors are charged to a selected energy, issue a control signal to trigger discharge and delivery of the electrical stimulation therapy through the output circuit by biasing two or more of the switches into a conducting state, wherein the generation of electrical stimulation therapy is controlled responsive to a result of the evaluated parameter.

10. The implantable medical system of claim 9, wherein the high side having a first switch and a third switch and the low side having a second switch and a fourth switch, wherein the first electrode terminal is coupled between the first and second switches and the second electrode terminal is coupled between the third and fourth switches.

11. The implantable medical system of claim 10, wherein each of the four interconnected switches comprises a solid-state semiconductor device.

12. The implantable medical system of claim 10, wherein the first and third switches comprise anode gated thyristors (AGT) and the second and fourth switches comprise insulated gate bipolar transistors (IGBT).

13. The implantable medical system of claim 9, wherein the electrical parameter is selected from one of a voltage and a current.

14. The implantable medical system of claim 9, further comprising a monitoring circuit coupled to the control circuit, the monitoring circuit being configured to measure the electrical parameter of the output circuit, wherein the monitoring circuit includes a voltage comparator configured to evaluate the electrical parameter of at least one component of the output circuit.

15. The implantable medical system of claim 9, further comprising a lead coupled to the housing, the lead including at least a first electrode coupled to the first electrode terminal.

16. The implantable medical system of claim 9, further comprising:
   at least a third electrode terminal, and
   a lead coupled to the housing, the lead including at least a first electrode and a second electrode coupled to the first and second electrode terminals respectively.

17. The implantable medical system of claim 9, further comprising a second electrode coupled to the housing, the second electrode being coupled to the second electrode terminal.

* * * * *